(12) United States Patent
Abbas

(10) Patent No.: US 12,728,244 B2
(45) Date of Patent: Sep. 8, 2026

(54) COMBINED PYELO-URETERAL STENT

(71) Applicants: Qatar Foundation for Education, Science and Community Development, Doha (QA); Sidra Medicine, Ar-Rayyan (QA)

(72) Inventor: Tariq Osman Saeed Abbas, Doha (QA)

(73) Assignees: Qatar Foundation for Education, Science and Community Development, Doha (QA); Hamad Medical Corporation, Doha (QA)

( * ) Notice: Subject to any disclaimer, the term of this patent is extended or adjusted under 35 U.S.C. 154(b) by 468 days.

(21) Appl. No.: 18/016,212

(22) PCT Filed: Jul. 14, 2021

(86) PCT No.: PCT/QA2021/050017
§ 371 (c)(1),
(2) Date: Jan. 13, 2023

(87) PCT Pub. No.: WO2022/015184
PCT Pub. Date: Jan. 20, 2022

(65) Prior Publication Data

US 2023/0264001 A1 Aug. 24, 2023

Related U.S. Application Data

(60) Provisional application No. 63/052,736, filed on Jul. 16, 2020.

(51) Int. Cl.
*A61M 27/00* (2006.01)
*A61F 2/04* (2013.01)
(Continued)

(52) U.S. Cl.
CPC ............ *A61M 27/008* (2013.01); *A61F 2/04* (2013.01); *A61F 2002/048* (2013.01);
(Continued)

(58) Field of Classification Search
CPC ........... A61M 27/008; A61M 25/0026; A61M 25/0045; A61M 25/0068; A61M 25/0152;
(Continued)

(56) References Cited

U.S. PATENT DOCUMENTS 6,364,868 B1 4/2002 Ikeguchi
6,524,268 B2 2/2003 Hayner et al.
(Continued)

FOREIGN PATENT DOCUMENTS

DE 4321792 A1 * 1/1995 ........ A61M 25/0017
WO WO-2018191099 A1 * 10/2018

OTHER PUBLICATIONS

International Search Report for related International Application No. PCT/QA2021/050017; action dated Jan. 20, 2022; (2 pages).
(Continued)

*Primary Examiner* — Adam Marcetich
(74) *Attorney, Agent, or Firm* — K&L Gates LLP

(57) ABSTRACT

A pyelo-ureteral stent is provided that combines the benefits of a stent having a lumen with the benefits of a lumen-less stent. In one example, the stent may be implanted in a patient for use during and after a pyeloplasty procedure. The provided stent includes a flexible tube having two separate lumens. Each lumen terminates prior to the stent's closed distal end, which enables a lumen-less ureteric limb at the stent's closed distal end. The lumen-less ureteric limb may have a smaller diameter than the rest of the stent, and may be positioned in a patient's ureter to bridge the pyeloplasty repair, thereby providing the benefits of a lumen-less stent. The flexible tube may be formed with at least one perforated
(Continued)

coil for the drainage of urine and/or blood. The stent may be removed from the patient without the use of a cystoscopic procedure.

20 Claims, 2 Drawing Sheets

(51) Int. Cl.
*A61M 25/00* (2006.01)
*A61M 25/01* (2006.01)

(52) U.S. Cl.
CPC ..... *A61M 25/0026* (2013.01); *A61M 25/0045* (2013.01); *A61M 25/0068* (2013.01); *A61M 25/0152* (2013.01); *A61M 2027/004* (2013.01); *A61M 2210/1082* (2013.01)

(58) Field of Classification Search
CPC .... A61M 2027/004; A61M 2210/1082; A61M 2025/0266; A61M 27/00; A61F 2/04; A61F 2002/048
See application file for complete search history.

(56) References Cited

U.S. PATENT DOCUMENTS

2002/0099332 A1* 7/2002 Slepian .................. A61F 2/958 604/103.02
2002/0188246 A1* 12/2002 Hayner ............ A61M 25/0017 604/48
2010/0280451 A1* 11/2010 Teeslink ............ A61M 25/1011 604/99.04
2012/0041419 A1* 2/2012 Blanchard .......... A61M 25/003 604/523
2014/0128793 A1* 5/2014 Whittam ............ A61M 27/008 604/9
2014/0135941 A1* 5/2014 Smouse ................... A61F 2/82 623/23.7
2015/0134073 A1 5/2015 Tang et al.
2015/0273120 A1* 10/2015 Zamarripa ........ A61M 25/1011 604/99.04
2016/0175559 A1* 6/2016 Gemborys ........ A61M 25/1011 604/103.03
2018/0117288 A1* 5/2018 Lindsay ............... A61M 27/00
2018/0235790 A1* 8/2018 Smouse ................... A61F 2/95
2019/0105465 A1* 4/2019 Erbey, II .................. A61F 2/04
2019/0105474 A1* 4/2019 Sheibley .............. A61M 29/02
2020/0061363 A1* 2/2020 Lindsay ............... A61M 39/10
2022/0142806 A1* 5/2022 Passman ............ A61M 3/0279

OTHER PUBLICATIONS

Written Opinion for related International Application No. PCT/QA2021/050017; action dated Jan. 20, 2022; (6 pages).
Written Opinion for related International Application No. PCT/QA21/50017; action dated Oct. 29, 2021; (6 pages).
International Search Report for related International Application No. PCT/QA21/50017; action dated Oct. 29, 2021; (2 pages).
Preliminary Report on Patentability for related International Application No. PCT/QA21/50017; action dated Oct. 29, 2021; (6 pages).
Abbas, et al.; "Double-Lumen Valve-Controlled Intra Operative Pyeloplasty Stent (VIPs)": A New Technology for Post-Pyeloplasty Stenting—Proof of Concept Study in a Preclinical Large Animal Model; National Library of Medine; Feb. 2020; (2 pages).

* cited by examiner

COMBINED PYELO-URETERAL STENT

CROSS-REFERENCE TO RELATED APPLICATIONS

The present application is a National Stage filing under 35 U.S.C. 371 of International Application No. PCT/QA2021/050017, filed on Jul. 14, 2021 which claims priority to and the benefit of U.S. Provisional Application 63/052,736, filed Jul. 16, 2020, the entirety of which is herein incorporated by reference.

TECHNICAL FIELD

The present relates generally to ureteral stents. More specifically, the present application provides a new and innovative pyelo-ureteral stent including dual lumens and a lumen-less distal portion.

BACKGROUND

A ureter is a tubular passageway in a body that conveys urine from a kidney to a bladder. Urine is transported through the ureter under the influence of hydrostatic pressure assisted by contractions of muscles located within the walls of the ureter. A urological condition that some patients experience is congenital uretero-pelvic junction (UPJ) obstruction. This obstruction or blockage occurs where the ureter attaches to the kidney. As a result, the flow of urine through the ureter decreases and fluid pressure inside the kidney increases.

Patients suffering from a UPJ obstruction must undergo pyeloplasty, a surgical reconstruction of the renal pelvis to relieve the blockage in the UPJ. The original ureter is surgically incised below the level of the obstruction (anastomosis line) and the abnormal section is removed. Then, the ureter is repositioned and attached to healthy renal pelvic tissue.

A stent may be placed into the ureter during surgery to bridge the pyeloplasty repair and help drain urine from the ureter until the patient heals. Pyelo-ureteral stents are designed to extend through the ureter to facilitate drainage from a kidney to the ureter during the pyeloplasty procedure area and usually for seven to ten days after the procedure. The stents generally include small diameter tubing of a biocompatible material. The pyelo-ureteral stent with an exteriorized end post-pyeloplasty can be used to aid in transfer of urine from the patient's kidney and ureter out of the patient, where post-operative edema or obstructions or other conditions may inhibit normal flow through the surgical anastomosis. Ideally, the stent should allow for flow of urine without migrating out of or further into the kidney, or out of or further into the bladder. Ureteral stents are positioned in the ureter by various procedures including, antegrade (percutaneous) placement, retrograde (cystoscopic) placement through the urethra, as well as by open ureterotomy or surgical placement in the ureter under direct visual placement.

With many typical stents, a physician must select what size stent to use based only on approximations of the patient's physiology. Other disadvantages of typical stents generally relate to high infection rates, vulnerability to dislodgement, incompatibility with laparoscopic or robotic pyeloplasty methods, a requirement of anesthesia for removal (e.g., completely internal stents, such as double-J stents), unreliability of postoperative contrast studies in the presence of the stent, difficulty in connecting with urine collection bags and syringes, and causing patient discomfort and bladder spasms due to the presence of the lower parts of the stents in the urinary bladder.

Further, when a typical pyelo-ureteral stent is used, it is generally necessary to insert a separate tube (e.g., Penrose drain) into the patient's body (below the stent) to serve as a drain for directing blood and/or urine from the perinephric space outside the body. The tube is covered with gauze to collect drainage flowing therefrom. Use of such a tube is often problematic, as it requires a separate incision into the body and additional stitches. Such drainage tubes also frequently slip out of the body. Further, as only gauze is used to receive the drainage from such tubes, it is difficult to determine exact amounts of bleeding and/or urine leakage post-surgery.

Accordingly, a need exists for a pyelo-ureteral stent that solves the above drawbacks.

SUMMARY

The present disclosure provides a new and innovative pyelo-ureteral stent that combines the benefits of a ureteric stent having a lumen with a lumen-less ureteric stent. The provided stent includes a first lumen and a second lumen that each terminate prior to a lumen-less ureteric limb. The lumen-less ureteric limb acts as a stent that promotes healing of the ureter after a pyeloplasty procedure. The lumen-less nature of the ureteric limb portion of the provided stent enables the ureteric limb to have a smaller diameter than if it were to have a lumen. It has been shown that a smaller diameter stent within the ureter may promote better ureteropelvic junction healing.

Additional benefits of the provided pyeloplasty stent include: (1) less siphoning of the bladder and contralateral kidney in case of unintentional intubation of the ipsilateral vesicoureteric junction or presence of ipsilateral Vesicoureteric reflux; (2) less complex and cheaper stent design; (3) no external pilot balloons; and (4) more user friendly design during post-operative contrast study.

In light of the technical features set forth herein, and without limitation, in a first aspect of the disclosure in the present application, which may be combined with any other aspect unless specified otherwise, a pyelo-ureteral stent includes a flexible tube including a closed distal end. The flexible tube is formed to include a perforated perinephric coil and a perforated renal coil with the perforated renal coil being closer to the closed distal end than the perforated perinephric coil. The flexible tube includes a first lumen extending from a first open proximal end and terminating between the perforated perinephric coil and the perforated renal coil. The flexible tube further includes a second lumen extending from a second open proximal end and terminating between the perforated renal coil and the closed distal end.

In a second aspect of the disclosure in the present application, which may be combined with any other aspect unless specified otherwise (e.g., the first aspect), the first open proximal end and the second open proximal end are each configured to fluidly connect to a bag or container for fluid collection.

In a third aspect of the disclosure in the present application, which may be combined with any other aspect unless specified otherwise (e.g., the first aspect), a portion of the flexible tube is solid throughout, the portion extending from a termination point of the second lumen to the closed distal end.

In a fourth aspect of the disclosure in the present application, which may be combined with any other aspect unless specified otherwise (e.g., the third aspect), the portion of the flexible tube has a diameter smaller than an outer diameter of a remaining portion of the flexible tube including the first and/or second lumen.

In a fifth aspect of the disclosure in the present application, which may be combined with any other aspect unless specified otherwise (e.g., the fourth aspect), the portion of the flexible tube has a diameter within the range of 50% to 70% of the outer diameter of the remaining portion of the flexible tube including the first and/or second lumen.

In a sixth aspect of the disclosure in the present application, which may be combined with any other aspect unless specified otherwise (e.g., the first aspect), the perforated perinephric coil straightens in response to applied tension and retains a coiled shape in the absence of applied tension.

In a seventh aspect of the disclosure in the present application, which may be combined with any other aspect unless specified otherwise (e.g., the first aspect), the perforated renal coil straightens in response to applied tension and retains a coiled shape in the absence of applied tension.

In an eighth aspect of the disclosure in the present application, which may be combined with any other aspect unless specified otherwise (e.g., the first aspect), the pyelo-ureteral stent further includes a coating on an outer surface of the flexible tube, the coating including at least one of a hydrophilic coating and an antibacterial coating.

In a ninth aspect of the disclosure in the present application, which may be combined with any other aspect unless specified otherwise (e.g., the eighth aspect), the coating is hydrophilic.

In a tenth aspect of the disclosure in the present application, which may be combined with any other aspect unless specified otherwise (e.g., the first aspect), a first portion of the flexible tube remains external to the patient upon a second portion of the flexible tube being implanted in the patient, and wherein the second portion of the flexible tube is constructed of a more malleable material than the first portion of the flexible tube.

In an eleventh aspect of the disclosure in the present application, which may be combined with any other aspect unless specified otherwise, a method of treating a patient with a pyelo-ureteral stent is provided. The pyelo-ureteral stent includes a flexible tube including a closed distal end. The flexible tube is formed to include a perforated perinephric coil and a perforated renal coil with the perforated renal coil being closer to the closed distal end than the perforated perinephric coil. The flexible tube includes a first lumen extending from a first open proximal end and terminating between the perforated perinephric coil and the perforated renal coil. The flexible tube further includes a second lumen extending from a second open proximal end and terminating between the perforated renal coil and the closed distal end. The method includes inserting the pyelo-ureteral stent through an abdominal wall of the patient and through the renal pelvic tissue of the patient. The perforated renal coil is positioned within a kidney of the patient such that the perforated perinephric coil is positioned outside of the kidney, the first open proximal end and the second open proximal end are positioned exterior to the patient, and the closed distal end is positioned within a ureter of the patient.

In a twelfth aspect of the disclosure in the present application, which may be combined with any other aspect unless specified otherwise (e.g., the eleventh aspect), a portion of the flexible tube from a termination point of the second lumen to the closed distal end is solid throughout, and at least some of the portion of the flexible tube is positioned within the ureter of the patient while the perforated renal coil is positioned within the kidney.

In a thirteenth aspect of the disclosure in the present application, which may be combined with any other aspect unless specified otherwise (e.g., the eleventh aspect), inserting the pyelo-ureteral stent includes applying tension to the flexible tube thereby straightening the perforated perinephric coil and the perforated renal coil as the pyelo-ureteral stent is inserted.

In a fourteenth aspect of the disclosure in the present application, which may be combined with any other aspect unless specified otherwise (e.g., the eleventh aspect), the method further includes draining blood from a perinephric space of the patient via the perforated perinephric coil, the first lumen, and the first open proximal end.

In a fifteenth aspect of the disclosure in the present application, which may be combined with any other aspect unless specified otherwise (e.g., the eleventh aspect), the method further includes draining urine from the kidney of the patient via the perforated renal coil, the second lumen, and the second open proximal end.

In a sixteenth aspect of the disclosure in the present application, which may be combined with any other aspect unless specified otherwise (e.g., the eleventh aspect), the method further includes removing the pyelo-ureteral stent by pulling the pyeo-ureteral stent through the abdominal wall of the patient.

In a seventeenth aspect of the disclosure in the present application, which may be combined with any other aspect unless specified otherwise (e.g., the eleventh aspect), the method further includes introducing contrast material into the kidney via the second lumen.

In an eighteenth aspect of the disclosure in the present application, which may be combined with any other aspect unless specified otherwise (e.g., the eleventh aspect), the closed distal end is positioned outside of a bladder of the patient.

In a nineteenth aspect of the disclosure in the present application, which may be combined with any other aspect unless specified otherwise (e.g., the eleventh aspect), positioning the renal coil within the kidney prevents the pyelo-ureteral stent from migrating after it is positioned.

In a twentieth aspect of the disclosure in the present application, which may be combined with any other aspect unless specified otherwise (e.g., the eleventh aspect), inserting the pyelo-ureteral stent includes laparoscopic or robotic deployment.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Figure 1:
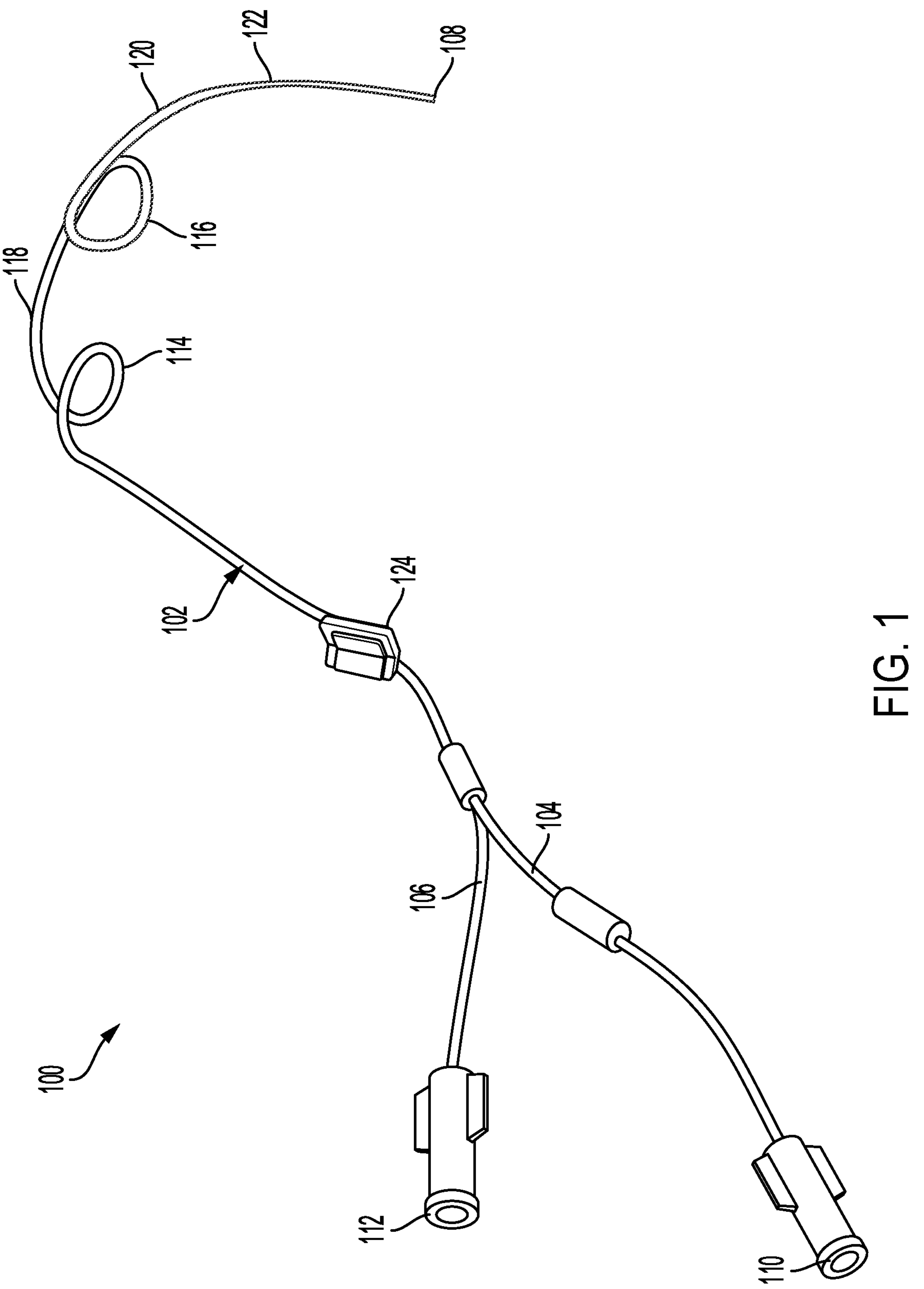
FIG. 1 illustrates a perspective view of a stent, according to an aspect of the present disclosure.

The present disclosure provides a new and innovative pyelo-ureteral stent that combines the benefits of a stent having a lumen with the benefits of a lumen-less stent. In one example implementation, the provided stent may be implanted in a patient for use during and after a pyeloplasty procedure. The provided stent is adapted to be percutaneously inserted and positioned within a patient. For instance, the provided stent may be implanted in an antegrade manner in the ureter percutaneously intraoperatively under direct vision. When implanted, the presently disclosed stent may provide drainage of urine from the kidney in the perioperative period and in the event of a blockage. The provided stent is also adapted to be removed from the patient without the use of a cystoscopic procedure.

The provided stent includes a flexible tube having two separate lumens. Each of the two separate lumens has its own open access point for the introduction (e.g., contrast material) or drainage (e.g., urine or blood) of fluid. The two lumens terminate at different positions along the flexible tube, as will be described. Opposite the access points for the lumens, the provided stent includes a closed distal end. Fluid cannot flow through the closed distal end.

The flexible tube may be formed to include at least one coil. A formed coil can be straightened when tension is applied, but contracts back to a coiled configuration once tension is released. A formed coil may include a plurality of holes (e.g., perforated) such that fluid may exit or enter the formed coil. In an example, the flexible tube may include two separate coils along its length. In such an example, a first lumen may be in fluid communication with the first coil and a second lumen may be in fluid communication with the second coil. The first lumen may terminate between the first coil and the second coil such that it is not in fluid communication with the second coil. The second lumen may bypass the first coil and terminate between the second coil and the closed end of the flexible tube.

When the provided stent is implanted in a patient, the second coil may be positioned within the patient's renal pelvis while the first coil is positioned in the patient's perinephric space. The second, or renal pelvis, coil helps retain the stent in position by preventing migration. Additionally, the perforations in each of the first, or perinephric, coil and the second coil help facilitate drainage (e.g., of urine) through the perforations and out the access point of either lumen. The coiled or generally circular formation of the coils may provide enhanced drainage.

With the second lumen terminating prior to the closed end of the flexible tube, the flexible tube includes a portion between the termination point of the second lumen and the closed end that is solid throughout (e.g., lumen-less). This solid, or lumen-less, portion of the flexible tube may be referred to as ureteric limb. The lumen-less ureteric limb may act as a stent that promotes ureter healing after a pyeloplasty procedure. One advantage provided by the lumen-less ureteric limb is that the lumen-less ureteric limb may have a smaller diameter than if it were to have a lumen. It has been shown that a smaller diameter stent within the ureter may promote better ureteropelvic junction healing. See F. Soria, et al., Ureteral Double-J Wire Stent Effectiveness after Endopylotomy: An Animal Model Study, Urologia Internationalis (April 2010).

The second lumen terminating prior to the ureteric limb also enables the presently disclosed stent to be provided without a pilot balloon. This is because contrast material injected through the second lumen must exit the stent through the holes in the second coil since the second lumen ends. There is no need for a pilot balloon to cause that to happen as with typical stents. Eliminating the pilot balloon enables a simpler and less-expensive stent as compared to typical stents having a pilot balloon. Further, typical stents with a lumen include a lumen that continues all the way through the stent to provide a path for urine to drain from the kidney to the bladder in the event of a blockage. The presently disclosed stent eliminates the need for such a drainage path since urine can be drained through the coil perforations to a bag or container outside the body if a blockage were to occur. As such, the provided stent provides the benefit of eliminating a pilot balloon without introducing drawbacks.

An additional advantage of the presently disclosed stent's closed distal end includes less siphoning of the bladder and contralateral kidney in the case of unintentional intubation of the ipsilateral vesico-ureteric junction or presence of ipsilateral vesico-ureteric reflux. Further, due to the stent's closed distal end, the stent provides a closed system, thereby decreasing the potential for bacterial migration and subsequent infections for the patient.

Accordingly, the provided stent provides the benefits of a smaller diameter stent within a patient's ureter while maintaining the benefits of urine drainage and contrast material injection, among other benefits.

FIG. 1 illustrates a perspective view of an example stent 100. The example stent 100 includes a flexible tube 102. In various aspects, the flexible tube 102 includes a first lumen 104 and a second lumen 106. The first lumen 104 may include an open proximal end 110. The second lumen 106 may include an open proximal end 112. Each of the open proximal ends 110 and 112 may be an access point for fluid introduction and/or drainage. Opposite the open proximal ends 110 and 112, the flexible tube 102 includes a closed distal end 108. Fluid may not flow through the closed distal end 108.

In various aspects, the flexible tube 102 may be formed to include a coil 114. Additionally or alternatively, the flexible tube 102 may be formed to include a coil 116. In the illustrated example, the flexible tube 102 is formed with both a coil 114 and coil 116. The coil 114 and the coil 116 may be formed to retain a coiled shape. For instance, each the coil 114 and the coil 116 can be straightened when tension is applied, but contract back to a coiled configuration once tension is released. In at least some aspects, the coils 114 and 116 may each be perforated such that each of the coils 114 and 116 include multiple holes.

In at least some aspects, the first lumen 104 extends from the open proximal end 110 and terminates between the coil 114 and the coil 116. For example, the first lumen 104 may terminate at the termination point 118, though in other examples, the first lumen 104 may terminate at other suitable positions between the coil 114 and the coil 116. The first lumen 104 may be in fluid communication with the coil 114 such that fluid may enter or exit the first lumen 104 through the perforations in the coil 114.

In at least some aspects, the second lumen 106 extends from the open proximal end 112 and terminates between the coil 116 and the closed distal end 108. For example, the second lumen may terminate at the termination point 120, though in other examples, the second lumen 106 may terminate at other suitable positions between the coil 116 and the closed distal end 108. The second lumen 106 may be in fluid communication with the coil 116 such that fluid may enter or exit the first lumen 106 through the perforations in the coil 116. Conversely, the second lumen 106 may bypass the coil 114 such that fluid passing through the perforations in the coil 114 does not enter the second lumen 106.

Between the termination point 120 of the second lumen 106 and the closed distal end 108, the stent 100 includes a ureteric limb 122. The ureteric limb 122 is lumen-less. Stated differently, the flexible tube 102 is solid throughout the ureteric limb 122 since each the first lumen 104 and the second lumen 106 have terminated prior to the ureteric limb 122. The ureteric limb 122 may act as a stent that promotes ureter healing. In at least some aspects, the ureteric limb 122 may have a smaller diameter than the remaining portion of the flexible tube 102. For instance, the lack of a lumen may enable the ureteric limb 122 to have a smaller diameter. In some examples, the ureteric limb 122 may have a diameter within the range of 50% to 70% of an outer diameter of the flexible tube 102. In some examples, the ureteric limb 122 may have a diameter within the range of 55% to 65% of the outer diameter of the flexible tube 102. In one example, the ureteric limb 122 may have a diameter equal to 60% of the outer diameter of the flexible tube 102. The smaller diameter of the ureteric limb 122 within the ureter may promote better ureteropelvic junction healing, as stated above.

In various aspects, the stent 100 may include a fixation component 124. The fixation component 124 may help secure the flexible tube 102 to a patient. In some instances, the fixation component 124 may be used with an adhesive.

The stent 100 can be constructed out of any material (e.g., silicone) suitable for ureteral catheters or stents. In some aspects, the entire stent 100, or at least the coil 116, may be constructed from one or more malleable materials. In some instances, a portion of the stent 100 that is positioned internally to the patient (e.g., between the fixation component 124 and the closed distal end 108) may be constructed of a softer or more malleable material than that used for the portion of the stent 100 that is positioned externally to the patient (e.g., between the fixation component 124 and the open proximal ends 110 and 112). In some aspects, the stent 100 can include a hydrophilic and/or antibacterial coating. In one embodiment, the stent 100 is constructed of an inert silicone material and includes a hydrophilic coating.

The example stent 100 is adapted to be percutaneously inserted and positioned within a patient. For instance, the provided stent may be implanted in an antegrade manner in the ureter percutaneously intraoperatively under direct vision. A surgeon may make an anastomosis incision between the patient's renal pelvis and ureter. The surgeon may then place the stent 100 into the kidney and ureter through the renal pelvis after passing through the abdominal wall. The surgeon may straighten the coil 114 and the coil 116 during insertion of the stent 100, after which the coil 114 and the coil 116 contract back to a coiled shape when in position. In various aspects, the stent 100 may be adapted for laparoscopic, robotic and/or open deployment.

Figure 2:
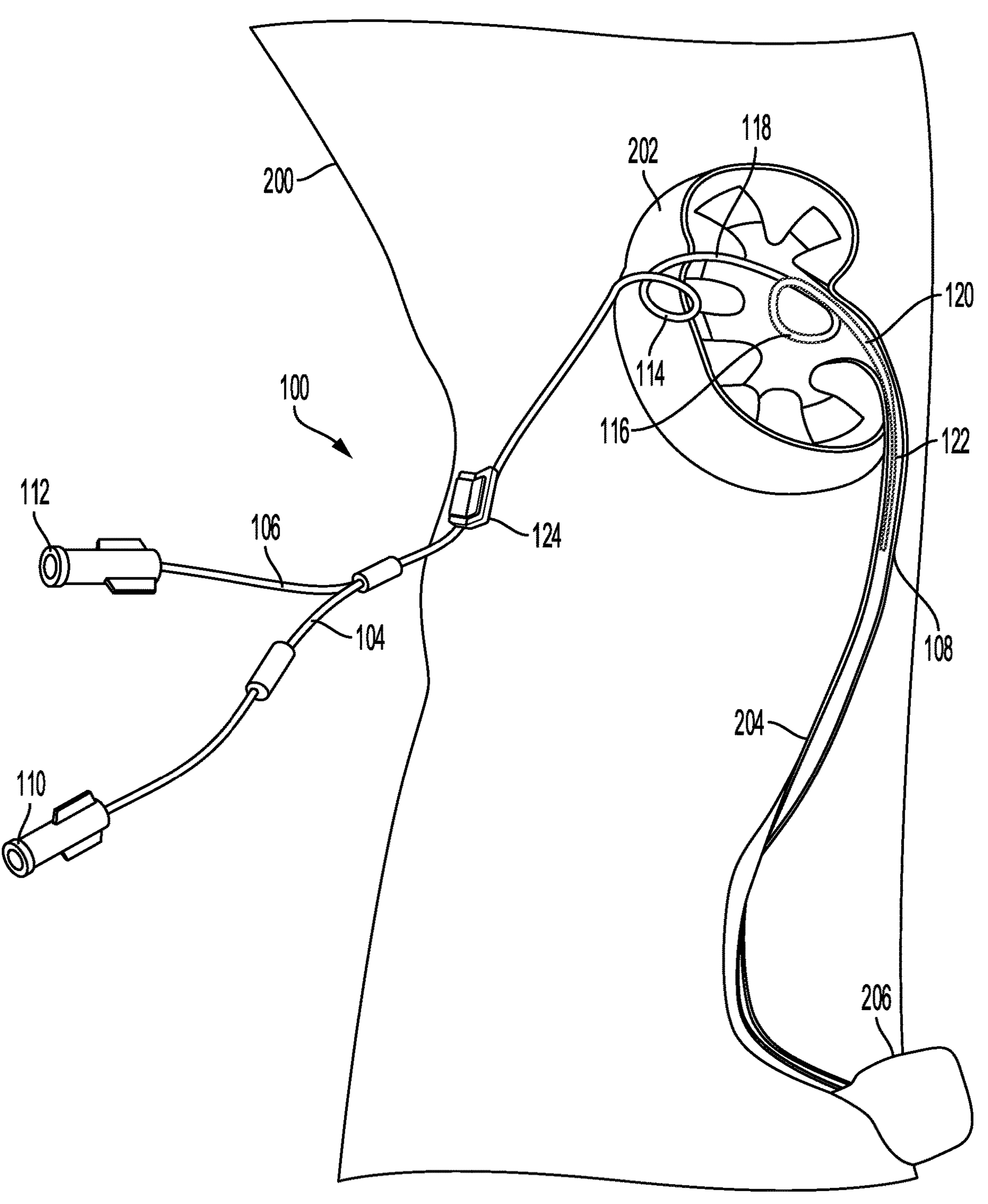
FIG. 2 illustrates the stent of FIG. 1 implanted within a patient, according to an aspect of the present disclosure.

FIG. 2 illustrates the stent 100 implanted within a patient 200. As shown, the lumen-less ureteric limb 122 is positioned in the ureter 204 to bridge the pyeloplasty repair without the distal end 108 extending into the bladder 206. The closed distal end 108 helps prevent the siphoning effect that might happen if the distal end of a typical stent with a lumen were to inadvertently reach the bladder through the vesico-ureteric junction. The stent 100 can be shortened if necessary, based on the anatomy of the patient 200, by cutting along the ureteric limb 122 of the stent 100. The surgeon may position the coil 116 in the renal pelvis of the kidney 202 as illustrated, which may help secure the stent 100 in position by preventing migration of the stent 100. The surgeon may position the coil 114 outside of the kidney 202 in the perinephric space as illustrated. The open proximal ends 110, 112 extend outside the abdominal wall of the patient 200. The fixation component 124 secures the stent 100 to the body wall of the patient 200 in this example.

In the illustrated implanted position, urine in the kidney 116 may drain through the perforations in the coil 116 and out the open proximal end 112 via the second lumen 106. For example, the open proximal end 112 may be connected to a bag or container for collecting the drained urine. As such, urine may be drained despite the distal end 108 of the flexible tube 102 being closed. Blood in the perinephric space, or urine that leaks outside of the kidney, may drain through the perforations in the coil 114 and out the open proximal end 110 via the first lumen 104. For instance, the open proximal end 110 may be connected to a bag or container for collecting the drained blood and/or urine. As such, the stent 100 obviates the need to use a separate perinephric drain, which would cause an extra wound or opening in the skin of the patient 200. Further, bedside removal of a typical perinephric drain typically causes discomfort and pain for a patient, and therefore by eliminating the need for a perinephric drain, the stent 100 eliminates this discomfort and pain for the patient. Additionally, unlike typical perinephric drains which measure output indirectly through weighing gauzes and dressings, the stent 100 permits direct and accurate perinephric drainage output by collecting the drainage output through the open proximal end 110 of the first lumen 104. The coiled or generally circular configuration of the coils 114 and 116 can help enhance drainage.

In at least some instances, a surgeon may introduce contrast material into the patient 200 via the stent 100 to assess the integrity of the pyeloplasty repair (e.g., whether there are leaks). Typical stents are constructed with a pilot balloon for the introduction of contrast material since typical stents with a lumen include a lumen that continues all the way through stent. The pilot balloon may be inflated to block the path of the contrast material so that it is introduced at the proper location. In contrast to typical stents with lumens, the second lumen 106 of the stent 100 terminates prior to the closed distal end 108, which therefore eliminates the need for a pilot balloon. Contrast material introduced through the open proximal end of the second lumen 106 will exit through the perforations in the coil 116 since it cannot continue past the termination point 120 of the second lumen 106. Eliminating the pilot balloon enables the stent 100 to be simpler and less expensive as compared to typical stents having a pilot balloon. The stent 100 can help increase the sensitivity of post-operative contrast studies for earlier diagnosis of a postoperative obstruction or leak at the anastomotic area.

When it is desired to remove the stent 100 from the patient 200, the stent 100 may be removed from the patient 200 by pulling on the proximal ends 110, 112 to pull the stent 100 through the abdominal wall of the patient 200. As the stent 100 is pulled, the coils 114 and 116 straighten to enable removal of the stent 100. The stent 100 therefore may be removed from the patient 200 without the use of a cystoscopic procedure.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A pyelo-ureteral stent comprising:

a flexible tube including a closed distal end, the flexible tube formed to include a perforated perinephric coil and a perforated renal coil, wherein the perforated renal coil is closer to the closed distal end than the perforated perinephric coil, wherein the flexible tube includes a first lumen extending from a first open proximal end and terminating between the perforated perinephric coil and the perforated renal coil, wherein the flexible tube includes a second lumen extending from a second open proximal end and terminating between the perforated renal coil and the closed distal end such that the second lumen terminates before the closed distal end, and wherein the perforated perinephric coil and the perforated renal coil are disposed between the closed distal end and a junction of the first lumen and the second lumen.

2. The pyelo-ureteral stent according to claim 1, wherein the first open proximal end and the second open proximal end are each configured to fluidly connect to a bag or container for fluid collection.

3. The pyelo-ureteral stent according to claim 1, wherein a portion of the flexible tube is solid throughout, the portion extending from a termination point of the second lumen to the closed distal end.

4. The pyelo-ureteral stent according to claim 3, wherein the portion of the flexible tube has a diameter smaller than an outer diameter of a remaining portion of the flexible tube including the first and/or second lumen.

5. The pyelo-ureteral stent according to claim 4, wherein the portion of the flexible tube has a diameter within the range of 50% to 70% of the outer diameter of the remaining portion of the flexible tube including the first and/or second lumen.

6. The pyelo-ureteral stent according to claim 1, wherein the perforated perinephric coil straightens in response to applied tension and retains a coiled shape in the absence of applied tension.

7. The pyelo-ureteral stent according to claim 1, wherein the perforated renal coil straightens in response to applied tension and retains a coiled shape in the absence of applied tension.

8. The pyelo-ureteral stent according to claim 1, further comprising a coating on an outer surface of the flexible tube, the coating including at least one of a hydrophilic coating and an antibacterial coating.

9. The pyelo-ureteral stent according to claim 8, wherein the coating is hydrophilic.

10. The pyelo-ureteral stent according to claim 1, wherein a first portion of the flexible tube remains external to the patient upon a second portion of the flexible tube being implanted in the patient, and wherein the second portion of the flexible tube is constructed of a more malleable material than the first portion of the flexible tube.

11. A method of treating a patient with a pyelo-ureteral stent including a flexible tube including a closed distal end, the flexible tube formed to include a perforated perinephric coil and a perforated renal coil, wherein the perforated renal coil is closer to the closed distal end than the perforated perinephric coil, wherein the flexible tube includes a first lumen extending from a first open proximal end and terminating between the perforated perinephric coil and the perforated renal coil, wherein the flexible tube includes a second lumen extending from a second open proximal end and terminating between the perforated renal coil and the closed distal end such that the second lumen terminates before the closed distal end, and wherein the perforated perinephric coil and the perforated renal coil are disposed between the closed distal end and a junction of the first lumen and the second lumen, the method comprising:

inserting the pyelo-ureteral stent through an abdominal wall of the patient and through the renal pelvic tissue of the patient; and positioning the perforated renal coil within a kidney of the patient such that the perforated perinephric coil is positioned outside of the kidney, the first open proximal end and the second open proximal end are positioned exterior to the patient, and the closed distal end is positioned within a ureter of the patient.

12. The method of claim 11, wherein a portion of the flexible tube from a termination point of the second lumen to the closed distal end is solid throughout, and wherein at least some of the portion of the flexible tube is positioned within the ureter of the patient while the perforated renal coil is positioned within the kidney.

13. The method of claim 11, wherein inserting the pyelo-ureteral stent includes applying tension to the flexible tube thereby straightening the perforated perinephric coil and the perforated renal coil as the pyelo-ureteral stent is inserted.

14. The method of claim 11, further comprising draining blood from a perinephric space of the patient via the perforated perinephric coil, the first lumen, and the first open proximal end.

15. The method of claim 11, further comprising draining urine from the kidney of the patient via the perforated renal coil, the second lumen, and the second open proximal end.

16. The method of claim 11, further comprising removing the pyelo-ureteral stent by pulling the pyelo-ureteral stent through the abdominal wall of the patient.

17. The method of claim 11, further comprising introducing contrast material into the kidney via the second lumen.

18. The method of claim 11, wherein the closed distal end is positioned outside of a bladder of the patient.

19. The method of claim 11, wherein positioning the renal coil within the kidney prevents the pyelo-ureteral stent from migrating after it is positioned.

20. The method of claim 11, wherein inserting the pyelo-ureteral stent includes laparoscopic or robotic deployment.

* * * * *